United States Patent
Demarais

(10) Patent No.: US 7,853,333 B2
(45) Date of Patent: *Dec. 14, 2010

(54) METHODS AND APPARATUS FOR MULTI-VESSEL RENAL NEUROMODULATION

(75) Inventor: Denise Demarais, Los Gatos, CA (US)

(73) Assignee: Ardian, Inc., Mountain View, CA (US)

( * ) Notice: Subject to any disclaimer, the term of this patent is extended or adjusted under 35 U.S.C. 154(b) by 323 days.

This patent is subject to a terminal disclaimer.

(21) Appl. No.: 11/451,728

(22) Filed: Jun. 12, 2006

(65) Prior Publication Data

US 2006/0235474 A1 Oct. 19, 2006

Related U.S. Application Data

(63) Continuation-in-part of application No. 11/129,765, filed on May 13, 2005, now Pat. No. 7,653,438.

(60) Provisional application No. 60/616,254, filed on Oct. 5, 2004, provisional application No. 60/624,793, filed on Nov. 2, 2004.

(51) Int. Cl.
*A61N 1/05* (2006.01)
(52) U.S. Cl. ...................................... 607/118
(58) Field of Classification Search .................. 607/2–3, 607/44, 62, 117, 118; 604/891.1
See application file for complete search history.

(56) References Cited

U.S. PATENT DOCUMENTS

| | | | |
|---|---|---|---|
| 2,130,758 A | 9/1938 | Rose | |
| 2,276,995 A | 3/1942 | Milinowski | |
| 2,276,996 A | 3/1942 | Milinowski | |
| 3,043,310 A | 7/1962 | Milinowski | |
| 3,127,895 A | 4/1964 | Kendall et al. | |
| 3,181,535 A | 5/1965 | Milinowski | |
| 3,270,746 A | 9/1966 | Kendall et al. | |
| 3,329,149 A | 7/1967 | Kendall et al. | |
| 3,522,811 A | 8/1970 | Schwartz et al. | |
| 3,563,246 A | 2/1971 | Puharich et al. | |
| 3,650,277 A | 3/1972 | Sjostrand et al. | |
| 3,670,737 A | 6/1972 | Pearo | |

(Continued)

FOREIGN PATENT DOCUMENTS

WO WO-2006/041881 4/2006

(Continued)

OTHER PUBLICATIONS

U.S. Appl. No. 10/408,665, filed Apr. 8, 2003, Levin et al.

(Continued)

*Primary Examiner*—Niketa I Patel
*Assistant Examiner*—Rex Holmes
(74) *Attorney, Agent, or Firm*—Perkins Coie LLP

(57) ABSTRACT

Methods and apparatus are provided for multi-vessel neuromodulation, e.g., via a pulsed electric field. Such multi-vessel neuromodulation may effectuate irreversible electroporation or electrofusion, necrosis and/or inducement of apoptosis, alteration of gene expression, action potential attenuation or blockade, changes in cytokine up-regulation and other conditions in target neural fibers. In some embodiments, the multi-vessel neuromodulation is applied to neural fibers that contribute to renal function. Such multi-vessel neuromodulation optionally may be performed bilaterally.

31 Claims, 6 Drawing Sheets

U.S. PATENT DOCUMENTS

| | | |
|---|---|---|
| 3,760,812 A | 9/1973 | Timm et al. |
| 3,774,620 A | 11/1973 | Hansjurgens |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,608,985 A | 9/1986 | Crish et al. |
| 4,649,936 A | 3/1987 | Ungar et al. |
| 4,671,286 A | 6/1987 | Renault |
| 4,674,482 A | 6/1987 | Waltonen et al. |
| 4,692,147 A | 9/1987 | Duggan |
| 4,715,852 A | 12/1987 | Reinicke et al. |
| 4,774,967 A | 10/1988 | Zanakis |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,057,318 A | 10/1991 | Magruder et al. |
| 5,058,584 A | 10/1991 | Bourgeois |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,304,120 A | 4/1994 | Crandell et al. |
| 5,304,206 A | 4/1994 | Baker et al. |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,351,394 A | 10/1994 | Weinberg |
| 5,358,514 A | 10/1994 | Schulman et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,472,406 A | 12/1995 | de la Torre et al. |
| 5,478,303 A | 12/1995 | Foley-Nolan et al. |
| 5,494,822 A | 2/1996 | Sadri |
| 5,498,238 A | 3/1996 | Shapland et al. |
| 5,499,971 A | 3/1996 | Shapland et al. |
| 5,507,724 A | 4/1996 | Hofmann et al. |
| 5,507,791 A | 4/1996 | Sit'ko |
| 5,531,778 A | 7/1996 | Maschino et al. |
| 5,540,730 A | 7/1996 | Terry, Jr. et al. |
| 5,540,734 A | 7/1996 | Zabara |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens |
| 5,584,863 A | 12/1996 | Rauch et al. |
| 5,589,192 A | 12/1996 | Okabe et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,792,187 A | 8/1998 | Adams |
| 5,800,464 A | 9/1998 | Kieval |
| 5,807,306 A | 9/1998 | Shapland et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,861,021 A | 1/1999 | Thome et al. |

| | | | | | | |
|---|---|---|---|---|---|---|
| 5,865,787 | A | 2/1999 | Shapland et al. | 6,508,774 | B1 | 1/2003 | Acker et al. |
| 5,871,449 | A | 2/1999 | Brown | 6,514,226 | B1 | 2/2003 | Levin et al. |
| 5,891,181 | A | 4/1999 | Zhu | 6,516,211 | B1 | 2/2003 | Acker et al. |
| 5,906,636 | A | 5/1999 | Casscells, III et al. | 6,522,926 | B1 | 2/2003 | Kieval et al. |
| 5,906,817 | A | 5/1999 | Moullier et al. | 6,522,932 | B1 | 2/2003 | Kuzma et al. |
| 5,913,876 | A | 6/1999 | Taylor et al. | 6,524,607 | B1 | 2/2003 | Goldenheim et al. |
| 5,916,154 | A | 6/1999 | Hobbs et al. | 6,534,081 | B2 | 3/2003 | Goldenheim et al. |
| 5,916,239 | A | 6/1999 | Geddes et al. | 6,536,949 | B1 | 3/2003 | Heuser |
| 5,919,187 | A | 7/1999 | Guglielmi et al. | 6,564,096 | B2 | 5/2003 | Mest |
| 5,924,997 | A | 7/1999 | Campbell | 6,571,127 | B1 | 5/2003 | Ben-Haim et al. |
| 5,928,272 | A | 7/1999 | Adkins et al. | 6,592,567 | B1 | 7/2003 | Levin et al. |
| 5,935,075 | A | 8/1999 | Casscells et al. | 6,599,256 | B1 | 7/2003 | Acker et al. |
| 5,944,710 | A | 8/1999 | Dev et al. | 6,600,954 | B2 | 7/2003 | Cohen et al. |
| 5,983,131 | A | 11/1999 | Weaver et al. | 6,600,956 | B2 | 7/2003 | Maschino et al. |
| 5,983,141 | A | 11/1999 | Sluijter et al. | 6,601,459 | B1 | 8/2003 | Jenni et al. |
| 6,006,134 | A | 12/1999 | Hill et al. | 6,605,084 | B2 | 8/2003 | Acker et al. |
| 6,010,613 | A | 1/2000 | Walters et al. | 6,615,071 | B1 | 9/2003 | Casscells, III et al. |
| 6,026,326 | A | 2/2000 | Bardy | 6,616,624 | B1 | 9/2003 | Kieval |
| 6,051,017 | A | 4/2000 | Loeb et al. | 6,620,151 | B2 | 9/2003 | Blischak et al. |
| 6,058,328 | A | 5/2000 | Levine et al. | 6,622,041 | B2 | 9/2003 | Terry, Jr. et al. |
| 6,058,331 | A | 5/2000 | King | 6,635,054 | B2 | 10/2003 | Fjield et al. |
| 6,073,048 | A | 6/2000 | Kieval et al. | 6,666,845 | B2 | 12/2003 | Hooper et al. |
| 6,077,227 | A | 6/2000 | Miesel et al. | 6,669,655 | B1 | 12/2003 | Acker et al. |
| 6,086,527 | A | 7/2000 | Talpade | 6,671,556 | B2 | 12/2003 | Osorio et al. |
| 6,122,548 | A | 9/2000 | Starkebaum et al. | 6,672,312 | B2 | 1/2004 | Acker |
| 6,123,718 | A | 9/2000 | Tu et al. | 6,676,657 | B2 | 1/2004 | Wood |
| 6,146,380 | A | 11/2000 | Racz et al. | 6,681,136 | B2 | 1/2004 | Schuler et al. |
| 6,161,048 | A | 12/2000 | Sluijter et al. | 6,684,105 | B2 | 1/2004 | Cohen et al. |
| 6,178,349 | B1 | 1/2001 | Kieval | 6,690,971 | B2 | 2/2004 | Schauerte et al. |
| 6,192,889 | B1 | 2/2001 | Morrish | 6,692,738 | B2 | 2/2004 | MacLaughlin et al. |
| 6,205,361 | B1 | 3/2001 | Kuzma et al. | 6,697,670 | B2 | 2/2004 | Chomenky et al. |
| 6,208,894 | B1 | 3/2001 | Schulman et al. | 6,718,208 | B2 | 4/2004 | Hill et al. |
| 6,214,032 | B1 | 4/2001 | Loeb et al. | 6,735,471 | B2 | 5/2004 | Hill et al. |
| 6,219,577 | B1 | 4/2001 | Brown, III et al. | 6,738,663 | B2 | 5/2004 | Schroeppel et al. |
| 6,238,702 | B1 | 5/2001 | Berde et al. | 6,749,598 | B1 | 6/2004 | Keren et al. |
| 6,245,026 | B1 | 6/2001 | Campbell et al. | 6,786,904 | B2 | 9/2004 | Doscher et al. |
| 6,246,912 | B1 * | 6/2001 | Sluijter et al. ............... 607/100 | 6,795,728 | B2 | 9/2004 | Chornenky et al. |
| 6,251,130 | B1 | 6/2001 | Dobak, III et al. | 6,845,267 | B2 | 1/2005 | Harrison et al. |
| 6,258,087 | B1 | 7/2001 | Edwards et al. | 6,850,801 | B2 | 2/2005 | Kieval et al. |
| 6,259,952 | B1 | 7/2001 | Sluijter et al. | 6,865,416 | B2 | 3/2005 | Dev et al. |
| 6,269,269 | B1 | 7/2001 | Ottenhoff et al. | 6,885,888 | B2 | 4/2005 | Rezai |
| 6,272,377 | B1 | 8/2001 | Sweeney et al. | 6,916,656 | B2 | 7/2005 | Walters et al. |
| 6,272,383 | B1 | 8/2001 | Grey et al. | 6,927,049 | B2 | 8/2005 | Rubinsky et al. |
| 6,280,377 | B1 | 8/2001 | Talpade | 6,939,345 | B2 | 9/2005 | KenKnight et al. |
| 6,287,304 | B1 | 9/2001 | Eggers et al. | 6,958,060 | B2 | 10/2005 | Mathiesen et al. |
| 6,287,608 | B1 | 9/2001 | Levin et al. | 6,972,013 | B1 | 12/2005 | Zhang et al. |
| 6,292,695 | B1 | 9/2001 | Webster, Jr. et al. | 6,978,174 | B2 | 12/2005 | Gelfand et al. |
| 6,304,777 | B1 | 10/2001 | Ben-Haim et al. | 6,985,774 | B2 | 1/2006 | Kieval et al. |
| 6,304,787 | B1 | 10/2001 | Kuzma et al. | 6,994,700 | B2 | 2/2006 | Elkins et al. |
| 6,306,423 | B1 | 10/2001 | Donovan et al. | 6,994,706 | B2 | 2/2006 | Chornenky et al. |
| 6,326,020 | B1 | 12/2001 | Kohane et al. | 7,054,685 | B2 | 5/2006 | Dimmer et al. |
| 6,326,177 | B1 | 12/2001 | Schoenbach et al. | 7,063,679 | B2 | 6/2006 | Maguire et al. |
| 6,334,069 | B1 | 12/2001 | George et al. | 7,081,114 | B2 | 7/2006 | Rashidi |
| 6,347,247 | B1 | 2/2002 | Dev et al. | 7,081,115 | B2 | 7/2006 | Taimisto |
| 6,353,763 | B1 | 3/2002 | George et al. | 7,083,614 | B2 | 8/2006 | Fjield et al. |
| 6,356,786 | B1 | 3/2002 | Rezai et al. | 7,122,019 | B1 | 10/2006 | Kesten et al. |
| 6,356,787 | B1 | 3/2002 | Rezai et al. | 7,191,015 | B2 | 3/2007 | Lamson et al. |
| 6,366,808 | B1 | 4/2002 | Schroeppel et al. | 2001/0044596 | A1 | 11/2001 | Jaafar |
| 6,366,815 | B1 | 4/2002 | Haugland et al. | 2002/0026222 | A1 | 2/2002 | Schauerte et al. |
| 6,393,324 | B2 | 5/2002 | Gruzdowich et al. | 2002/0026228 | A1 | 2/2002 | Schauerte |
| 6,400,982 | B2 | 6/2002 | Sweeney et al. | 2002/0032468 | A1 | 3/2002 | Hill et al. |
| 6,405,079 | B1 | 6/2002 | Ansarinia | 2002/0038137 | A1 | 3/2002 | Stein |
| 6,405,732 | B1 | 6/2002 | Edwards et al. | 2002/0040204 | A1 | 4/2002 | Dev et al. |
| 6,415,183 | B1 | 7/2002 | Scheiner et al. | 2002/0045853 | A1 | 4/2002 | Dev et al. |
| 6,415,187 | B1 | 7/2002 | Kuzma et al. | 2002/0072782 | A1 | 6/2002 | Osorio et al. |
| 6,438,423 | B1 | 8/2002 | Rezai et al. | 2002/0107553 | A1 | 8/2002 | Hill et al. |
| 6,442,424 | B1 | 8/2002 | Ben-Haim et al. | 2002/0116030 | A1 | 8/2002 | Rezai |
| 6,449,507 | B1 | 9/2002 | Hill et al. | 2002/0120304 | A1 | 8/2002 | Mest |
| 6,450,942 | B1 | 9/2002 | Lapanashvili et al. | 2002/0165586 | A1 | 11/2002 | Hill et al. |
| 6,461,314 | B1 | 10/2002 | Pant et al. | 2002/0169413 | A1 | 11/2002 | Keren et al. |
| 6,464,687 | B1 | 10/2002 | Ishikawa et al. | 2002/0177846 | A1 | 11/2002 | Mulier et al. |
| 6,473,644 | B1 | 10/2002 | Terry, Jr. et al. | 2002/0183684 | A1 | 12/2002 | Dev et al. |
| 6,482,619 | B1 | 11/2002 | Rubinsky et al. | 2002/0188325 | A1 | 12/2002 | Hill et al. |

| | | |
|---|---|---|
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0040774 A1 | 2/2003 | Terry et al. |
| 2003/0045909 A1 | 3/2003 | Gross et al. |
| 2003/0060848 A1* | 3/2003 | Kieval et al. ............ 607/2 |
| 2003/0060857 A1 | 3/2003 | Perrson et al. |
| 2003/0060858 A1 | 3/2003 | Kieval et al. |
| 2003/0100924 A1 | 5/2003 | Foreman et al. |
| 2003/0120270 A1 | 6/2003 | Acker |
| 2003/0150464 A1 | 8/2003 | Casscells |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0236443 A1 | 12/2003 | Cespedes et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0220511 A1 | 11/2004 | Scott et al. |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080459 A1 | 4/2005 | Jacobson et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2005/0288730 A1 | 12/2005 | Deem et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0089674 A1 | 4/2006 | Walters et al. |
| 2006/0100667 A1 | 5/2006 | Machado et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0229677 A1 | 10/2006 | Moffitt et al. |
| 2006/0265015 A1 | 11/2006 | Demarais et al. |

FOREIGN PATENT DOCUMENTS

| | | |
|---|---|---|
| WO | WO-2007/035537 | 3/2007 |
| WO | WO-2007/078997 | 7/2007 |
| WO | WO-2007/146834 | 12/2007 |

OTHER PUBLICATIONS

U.S. Appl. No. 10/900,199, filed Jul. 28, 2004, Gelfand.
U.S. Appl. No. 11/129,765, filed May 13, 2005, Deem.
U.S. Appl. No. 11/133,925, filed May 20, 2005, Gelfand.
U.S. Appl. No. 11/144,173, filed Jun. 3, 2005, Levin et al.
U.S. Appl. No. 11/144,298, filed Jun. 3, 2005, Levin et al.
U.S. Appl. No. 11/145,122, filed Jun. 3, 2005, Levin et al.
U.S. Appl. No. 11/189,563, filed Jul. 25, 2005, Deem.
U.S. Appl. No. 11/233,814, Denise Demarais.
U.S. Appl. No. 11/252,462, Denise Demarais.
U.S. Appl. No. 11/266,993, Demarais.
U.S. Appl. No. 11/324,188, Denise Demarais.
U.S. Appl. No. 11/363,867, Denise Demarais.
U.S. Appl. No. 11/368,553, Demarais et al.
U.S. Appl. No. 11/368,577, Demarais.
U.S. Appl. No. 11/368,809, Denise Demarais.
U.S. Appl. No. 11/368,836, Demarais.
U.S. Appl. No. 11/368,949, Denise Demarais.
U.S. Appl. No. 11/368,971, Denise Demarais.
U.S. Appl. No. 11/403,329, Demarais et al.
U.S. Appl. No. 60/236,420, Harrison et al.
U.S. Appl. No. 60/370,190.
U.S. Appl. No. 60/408,665.
U.S. Appl. No. 60/415,575.
U.S. Appl. No. 60/442,970.
U.S. Appl. No. 11/504,117, Demarais et al.
U.S. Appl. No. 11/599,649, Demarais et al.
U.S. Appl. No. 11/599,723, Demarais et al.
U.S. Appl. No. 11/599,882, Demarais et al.
U.S. Appl. No. 11/599,890, Demarais et al.
U.S. Appl. No. 11/688,178, Levin et al.
Bello-Reuss, E. et al., "Effect of renal sympathetic nerve stimulation on proximal water and sodium reabsorption," J Clin Invest, 1976;57:1104-1107.
Bhandari, A. and Ellias, M., "Loin pain hematuria syndrome: Pain control with RFA to the Splanchanic plexus," The Pain Clinic, 2000, vol. 12, No. 4, pp. 323-327.
Final Office Action; U.S. Appl. No. 11/233,814; Mailed on Jan. 29, 2009, 11 pages.

Final Office Action; U.S. Appl. No. 11/363,867; Mailed on May 1, 2009, 8 pages.

International Search Report and Written Opinion, PCT/US05/35757, Mailed on Dec. 27, 2006, Applicant: Ardian, Inc., 8 pages.

International Search Report and Written Opinion, PCT/US06/36120, Mailed on Jun. 25, 2008, Applicant: Ardian, Inc., 10 pages.

International Search Report and Written Opinion, PCT/US06/48822, Mailed on Aug. 15, 2008, Applicant: Ardian, Inc., 12 pages.

International Search Report and Written Opinion, PCT/US07/70799, Mailed on Jul. 2, 2008, Applicant: Ardian, Inc., 7 pages.

Non-Final Office Action; U.S. Appl. No. 11/129,765; Mailed on May 18, 2007, 10 pages.

Non-Final Office Action; U.S. Appl. No. 11/129,765; Mailed on Sep. 10, 2007, 5 pages.

Non-Final Office Action; U.S. Appl. No. 11/129,765; Mailed on Oct. 6, 2006, 30 pages.

Non-Final Office Action; U.S. Appl. No. 11/144,173; Mailed on Apr. 5, 2007, 33 pages.

Non-Final Office Action; U.S. Appl. No. 11/144,173; Mailed on Sep. 10, 2007, 5 pages.

Non-Final Office Action; U.S. Appl. No. 11/145,122; Mailed on Apr. 11, 2007, 33 pages.

Non-Final Office Action; U.S. Appl. No. 11/145,122; Mailed on Sep. 10, 2007, 5 pages.

Non-Final Office Action; U.S. Appl. No. 11/233,814; Mailed on Jun. 7, 2008, 12 pages.

Non-Final Office Action; U.S. Appl. No. 11/363,867; Mailed on Sep. 25, 2008, 10 pages.

Osborn, et al., "Effect of renal nerve stimulation on renal blood flow autoregulation and antinatriuresis during reductions in renal perfusion pressure," in Proceedings of the Society for Experimental Biology and Medicine, vol. 168, 77-81, 1981. (Abstract).

* cited by examiner

METHODS AND APPARATUS FOR MULTI-VESSEL RENAL NEUROMODULATION

REFERENCE TO RELATED APPLICATIONS

The present application is a Continuation-In-Part application of co-pending U.S. patent application Ser. No. 11/129,765, filed on May 13, 2005, which claims the benefit of U.S. Provisional Application Nos. (a) 60/616,254, filed on Oct. 5, 2004, and (b) 60/624,793, filed on Nov. 2, 2004.

All of these applications are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for neuromodulation. In some embodiments, the present invention relates to methods and apparatus for achieving renal neuromodulation.

BACKGROUND

Congestive Heart Failure ("CHF") is a condition that occurs when the heart becomes damaged and reduces blood flow to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidneys. Such high levels of renal sympathetic nerve activity lead to decreased removal of water and sodium from the body, as well as increased secretion of renin. Increased renin secretion leads to vasoconstriction of blood vessels supplying the kidneys which causes decreased renal blood flow. Reduction of sympathetic renal nerve activity, e.g., via denervation, may reverse these processes.

Applicants have previously described methods and apparatus for treating renal disorders by applying a pulsed electric field to neural fibers that contribute to renal function. See, for example, Applicants' co-pending U.S. patent application Ser. No. 11/129,765, filed on May 13, 2005, and Ser. No. 11/189,563, filed on Jul. 25, 2005, both of which are incorporated herein by reference in their entireties. A pulsed electric field ("PEF") may initiate denervation or other renal neuromodulation via irreversible electroporation, electrofusion or other processes. The PEF may be delivered from apparatus positioned intravascularly, extravascularly, intra-to-extravascularly or a combination thereof. Additional methods and apparatus for achieving renal neuromodulation via localized drug delivery (such as by a drug pump or infusion catheter), a stimulation electric field, or other modalities are described, for example, in co-owned and co-pending U.S. patent application Ser. No. 10/408,665, filed Apr. 8, 2003, and U.S. Pat. No. 6,978,174, both of which are incorporated herein by reference in their entireties.

Electrofusion generally refers to the fusion of neighboring cells induced by exposure to an electric field. Contact between target neighboring cells for the purposes of electrofusion may be achieved in a variety of ways, including, for example, via dielectrophoresis. In tissue, the target cells may already be in contact, thus facilitating electrofusion.

Electroporation and electropermeabilization generally refer to methods of manipulating the cell membrane or intracellular apparatus. For example, the porosity of a cell membrane may be increased by inducing a sufficient voltage across the cell membrane through short, high-voltage pulses. The extent of porosity in the cell membrane (e.g., size and number of pores) and the duration of effect (e.g., temporary or permanent) are a function of multiple variables, such as the field strength, pulse width, duty cycle, electric field orientation, cell type or size and/or other parameters.

Cell membrane pores will generally close spontaneously upon termination of relatively lower strength electric fields or relatively shorter pulse widths (herein defined as "reversible electroporation"). However, each cell or cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes.

A potential challenge of using intravascular PEF systems for treating renal disorders is to selectively electroporate target cells without affecting other cells. For example, it may be desirable to irreversibly electroporate renal nerve cells that travel along or in proximity to renal vasculature, but it may not be desirable to damage the smooth muscle cells of which the vasculature is composed. As a result, an overly aggressive course of PEF therapy may persistently injure the renal vasculature, but an overly conservative course of PEF therapy may not achieve the desired renal neuromodulation.

Applicants have previously described methods and apparatus for monitoring tissue impedance or conductivity to determine the effects of pulsed electric field therapy, e.g., to determine an extent of electroporation and/or its degree of irreversibility. See, for example, Applicant's co-pending U.S. patent application Ser. No. 11/233,814, filed Sep. 23, 2005, which is incorporated herein by reference in its entirety.

Pulsed electric field electroporation of tissue causes a decrease in tissue impedance and an increase in tissue conductivity. If induced electroporation is reversible, tissue impedance and conductivity should approximate baseline levels upon cessation of the pulsed electric field. However, if electroporation is irreversible, impedance and conductivity changes should persist after terminating the pulsed electric field. Thus, monitoring the impedance or conductivity of target and/or non-target tissue may be utilized to determine the onset of electroporation and to determine the type or extent of electroporation. Furthermore, monitoring data may be used in one or more manual or automatic feedback loops to control the electroporation.

In view of the foregoing, it would be desirable to provide additional methods and apparatus for achieving renal neuromodulation.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which.

DETAILED DESCRIPTION

A. Overview

Figure 1:
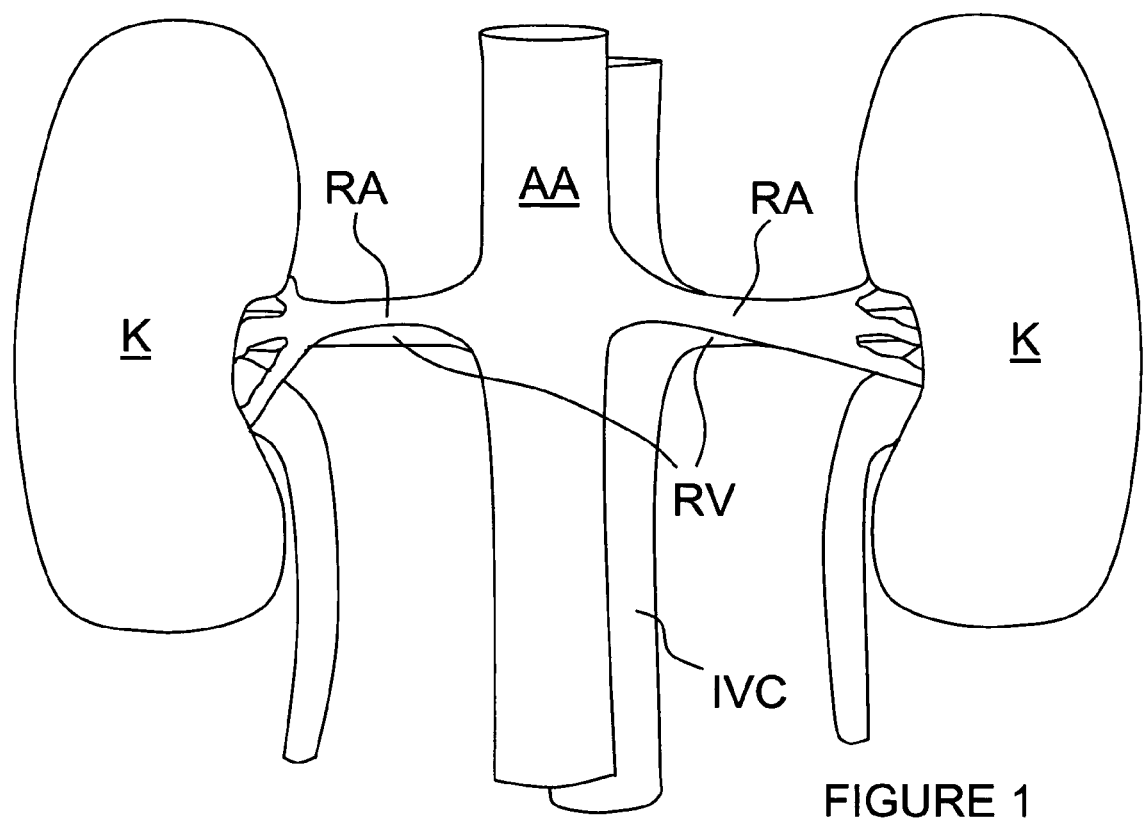
FIG. 1 is a schematic view illustrating human renal anatomy.

The methods and apparatus of the present invention may be used to modulate neural fibers that contribute to renal function and may exploit any suitable neuromodulatory techniques that will achieve the desired neuromodulation. Several embodiments of the present invention are methods and apparatus for neuromodulation via a pulsed electric field ("PEF"), a stimulation electric field, localized drug delivery, high frequency ultrasound, thermal techniques, athermal techniques, combinations thereof, and/or other techniques. Neuromodulation may, for example, effectuate irreversible electroporation or electrofusion, necrosis and/or inducement of apoptosis, alteration of gene expression, action potential blockade or attenuation, changes in cytokine up-regulation and other conditions in target neural fibers. In several embodiments, neuromodulation is achieved via multi-vessel methods and apparatus with neuromodulatory elements positioned proximate to or within multiple vessels and/or multiple branches of a single vessel.

In some patients, when the multi-vessel neuromodulatory methods and apparatus of the present invention are applied to renal nerves and/or other neural fibers that contribute to renal neural functions, the applicants believe that the neuromodulation may directly or indirectly increase urine output, decrease plasma renin levels, decrease tissue (e.g., kidney) and/or urine catecholamines, cause renal catecholamine (e.g., norepinephrine) spillover, increase urinary sodium excretion, and/or control blood pressure. Furthermore, applicants believe that these or other changes may prevent or treat congestive heart failure, hypertension, acute myocardial infarction, end-stage renal disease, contrast nephropathy, other renal system diseases, and/or other renal or cardio-renal anomalies. The methods and apparatus described herein may be used to modulate efferent and/or afferent nerve signals.

Renal neuromodulation preferably is performed in a bilateral fashion such that neural fibers contributing to renal function of both the right and left kidneys are modulated. Bilateral renal neuromodulation may provide enhanced therapeutic effect in some patients as compared to renal neuromodulation performed unilaterally, i.e. as compared to renal neuromodulation performed on neural tissue innervating a single kidney. In some embodiments, concurrent modulation of neural fibers that contribute to both right and left renal function may be achieved; while in other embodiments, modulation of the right and left neural fibers may be sequential. Bilateral renal neuromodulation may be continuous or intermittent, as desired.

When utilizing an electric field to achieve desired renal neuromodulation, the electric field parameters may be altered and combined in any suitable combination. Such parameters can include, but are not limited to, voltage, field strength, frequency, pulse width, pulse duration, the shape of the pulse, the number of pulses and/or the interval between pulses (e.g., duty cycle), etc. For example, when utilizing a pulsed electric field, suitable field strengths can be up to about 10,000 V/cm and suitable pulse widths can be up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, or combinations. The field includes at least one pulse, and in many applications the field includes a plurality of pulses. Suitable pulse intervals include, for example, intervals less than about 10 seconds. These parameters are provided as suitable examples and in no way should be considered limiting.

To better understand the structures of devices of the present invention and the methods of using such devices for renal neuromodulation, it is instructive to examine the renal anatomy in humans.

B. Selected Embodiments of Methods for Neuromodulation

Figure 2:
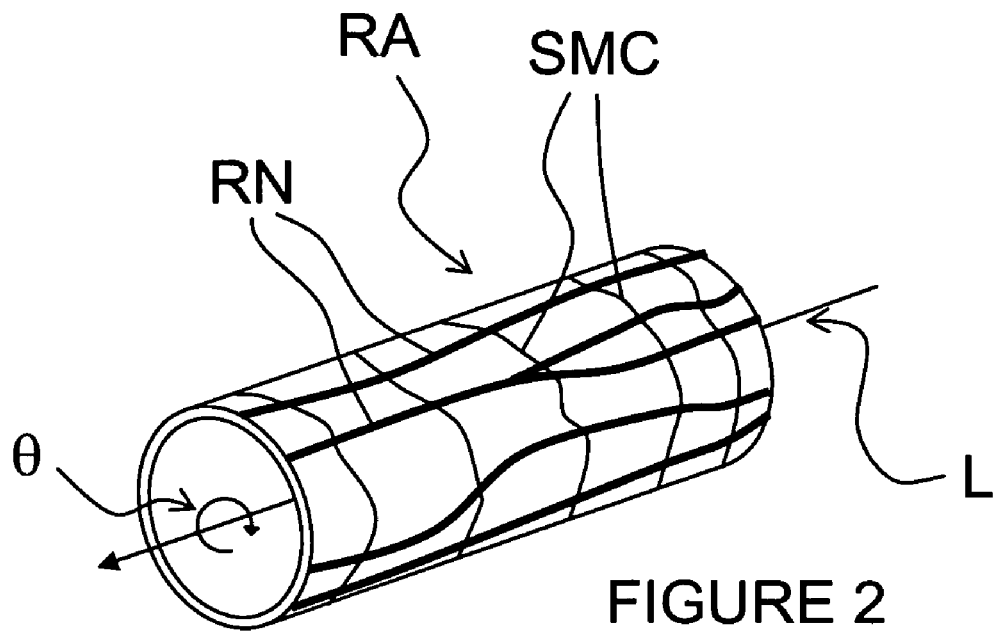
FIG. 2 is a schematic isometric detail view showing the location of the renal nerves relative to the renal artery.

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN generally extending longitudinally along the lengthwise dimension L of renal artery RA, generally within the adventitia of the artery. The renal artery RA has smooth muscle cells SMC that generally surround the arterial circumference and spiral around the angular axis θ of the artery. The smooth muscle cells of the renal artery accordingly have a lengthwise or longer dimension extending relatively transverse (i.e., non-parallel) to the lengthwise dimension of the renal artery. The misalignment of the lengthwise dimensions of the renal nerves and the smooth muscle cells is defined as "cellular misalignment."

Figure 3A:
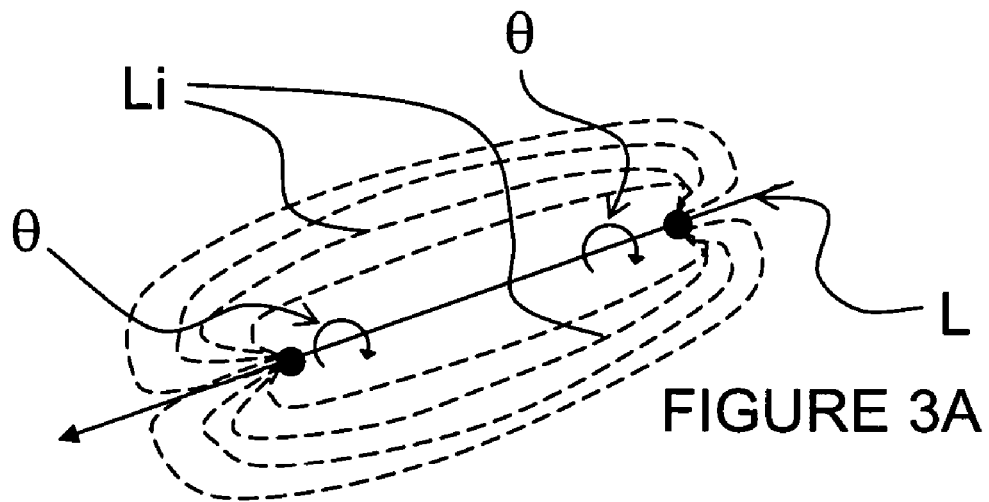
FIGS. 3A and 3B are schematic isometric and end views, respectively, illustrating orienting of an electric field for selectively affecting renal nerves.
Figure 3B:
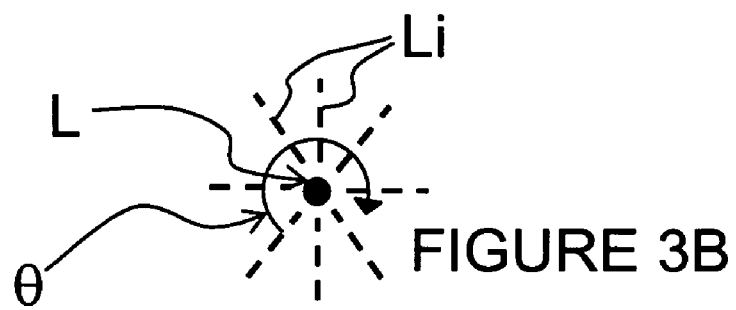

Referring to FIGS. 3A and 3B, the cellular misalignment of the renal nerves and the smooth muscle cells optionally may be exploited to selectively affect renal nerve cells with reduced effect on smooth muscle cells. More specifically, because larger cells require a lower electric field strength to exceed the cell membrane irreversibility threshold voltage or energy for irreversible electroporation, embodiments of the present invention optionally may be configured to align at least a portion of an electric field with or near the longer dimensions of the cells to be affected. In specific embodiments, the device has a bipolar electrode pair positioned in different vessels and configured to create an electrical field aligned with or near the lengthwise dimension L of the renal artery RA to preferentially affect the renal nerves RN. By aligning an electric field so that the field preferentially aligns with the lengthwise aspect of the cell rather than the diametric or radial aspect of the cell, lower field strengths may be used to affect target neural cells, e.g., to necrose or fuse the target cells, to induce apoptosis, to alter gene expression, to attenuate or block action potentials, to change cytokine up-regulation and/or to induce other suitable processes. This is expected to reduce total energy delivered to the system and to mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning a pulsed electric field ("PEF") with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIGS. 3A and 3B, applying a PEF with propagation lines Li generally aligned with the longitudinal dimension L of the renal artery RA is expected to preferentially cause electroporation (e.g., irreversible electroporation), electrofusion or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment θ through a range of 0°-360°.

A PEF system placed within and/or in proximity to the wall of the renal artery may propagate an electric field having a longitudinal portion that is aligned to run with the longitudinal dimension of the artery in the region of the renal nerves RN and the smooth muscle cells SMC of the vessel wall so that the wall of the artery remains at least substantially intact while the outer nerve cells are destroyed, fused or otherwise affected. Monitoring elements optionally may be utilized to assess an extent of, e.g., electroporation, induced in renal nerves and/or in smooth muscle cells, as well as to adjust PEF parameters to achieve a desired effect.

C. Embodiments of Systems and Methods for Multi-Vessel Neuromodulation

Figure 4:
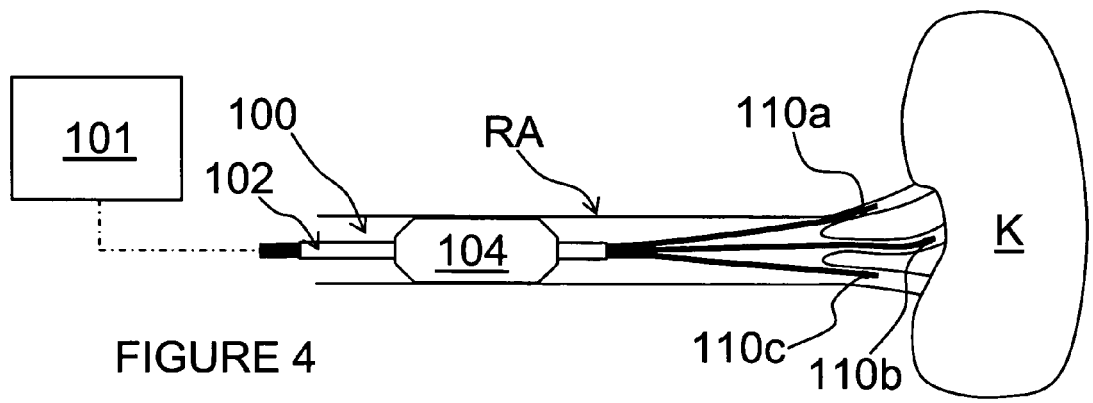
FIG. 4 is a schematic side view, partially in section, illustrating an example of a multi-vessel method and apparatus for renal neuromodulation.

With reference to FIGS. 4-7, examples of multi-vessel PEF systems and methods are described. FIG. 4 shows one embodiment of a multi-vessel pulsed electric field apparatus 100 that includes multiple electrodes 110 configured to deliver a pulsed electric field to renal neural fibers to achieve renal neuromodulation. The electrodes 110 are positioned intravascularly within multiple vessels that branch off from main renal artery RA. The apparatus 100 may further comprise a catheter 102 through which the electrodes 110 may be delivered to vessel branchings. The catheter also may comprise a positioning element 104, as described hereinafter. Applicants have previously described intravascular PEF systems, for example, in co-pending U.S. patent application Ser. No. 11/129,765, filed May 13, 2005, which has been incorporated herein by reference in its entirety.

The proximal section of the apparatus 100 generally has one or more electrical connectors to couple the electrodes 110 to a pulse generator 101. The pulse generator is located external to the patient. The generator, as well as any of the electrode embodiments described herein, may be utilized with any embodiment of the present invention described hereinafter for delivery of a PEF with desired field parameters. It should be understood that electrodes of embodiments described hereinafter may be electronically connected to the generator even though the generator is not explicitly shown or described with each embodiment.

As seen in FIG. 4, the electrodes 110 are positioned in multiple vessels that branch off from a renal artery RA in the vicinity of a kidney K. The electrical signals may be applied independently and/or dynamically to each of the electrodes 110 to facilitate a monopolar and/or a bipolar energy delivery between/among any of the electrodes and/or an external ground pad (not shown). A ground pad, for example, may be attached externally to the patient's skin (e.g., to the patient's leg, flank, back or side) when one or more of the electrodes deliver monopolar energy. Additionally or alternatively, the optional ground pad may be attached externally to the patient adjacent to the targeted kidney to induce desired directionality in a monopolar electrical field. A combination bipolar and monopolar PEF treatment may be more effective than a stand-alone bipolar and/or a stand-alone monopolar treatment for some patients or for some indications.

It is expected that applying a bipolar field between a desired pair of the electrodes 110 positioned in different vessels, e.g., between the electrode 110a and the electrode 110b, may modulate the function of the target neural fibers in a manner that at least partially denervates the patient's kidney. The electrodes 110a and 110b (as well as the electrodes 110b and 110c) optionally may be laterally spaced from one another along the lengthwise dimension of the renal artery RA, which is expected to preferentially align an electric field delivered between the electrodes with the target neural fibers. The neuromodulation may be achieved thermally or substantially athermally. Such PEF therapy may alleviate clinical symptoms of CHF, hypertension, renal disease, myocardial infarction, contrast nephropathy and/or other renal or cardio-renal diseases for a period of months (e.g., potentially up to six months or more). This time period may be sufficient to allow the body to heal to potentially reduce the risk of CHF onset after an acute myocardial infarction and mitigate the need for subsequent re-treatment. Alternatively, as symptoms reoccur, or at regularly scheduled intervals, the patient can return to the physician for a repeat therapy.

The effectiveness of the initial therapy, and thus the potential need for repeating the therapy, can be evaluated by monitoring several different physiologic parameters. For example, plasma renin levels, renal catecholamine (e.g., norepinephrine) spillover, urine catecholamines, or other neurohormones that are indicative of increased sympathetic nervous activity can provide an indication of the extent of denervation. Additionally or alternatively, a nuclear imaging test, such as a test utilizing 131-Iodine metaiodobenzylguanidine ("MIBG"), may be performed to measure a degree of adrenergic innervation. As another option, imaging may be performed with Technetium-99m mercaptoacetylglycine ("Tc-99m MAG3") to evaluate renal function. Alternatively, provocative maneuvers known to increase sympathetic nervous activity, such as head-out water immersion testing, may be conducted to determine the need for repeat therapy.

Embodiments of the PEF system 100 optionally may comprise one or more positioning elements for centering or otherwise positioning the system or parts of the system within the patient's vasculature. The positioning element may, for example, comprise inflatable balloons and/or expandable wire baskets or cages. The positioning element optionally may comprise an impedance-altering element configured to alter impedance within the patient's vasculature to better direct an applied electric field across the vessel wall to target neural fibers. When the positioning element is a balloon, it may temporarily block blood flow and thereby alter the impedance within the patient's vessel. Additionally or alternatively, the positioning element may further comprise one or more electrodes. In one embodiment, a balloon positioning element has a conductive exterior and/or is fabricated from a conductive polymer that may be used as an electrode in a multi-vessel PEF system.

In FIG. 4, the PEF system 100 comprises an expandable positioning element 104 coupled to the catheter 102. The positioning element 104 is configured for delivery and retrieval from a treatment site in a reduced profile delivery configuration, and for expansion at the treatment site to the deployed configuration of FIG. 4. With the positioning element in the fully expanded, deployed configuration of FIG. 4, impedance characteristics within the renal artery RA may be altered, and/or delivery and retrieval of the electrode(s) 110 to the multiple vessel branchings may be facilitated.

As discussed previously, it is expected that a multi-vessel PEF therapy may effectuate one or more of the following: irreversible electroporation or electrofusion; necrosis and/or inducement of apoptosis; alteration of gene expression; action potential blockade or attenuation; changes in cytokine up-regulation; and other conditions in target neural fibers. In some patients, when such neuromodulatory methods and apparatus are applied to renal nerves and/or other neural fibers that contribute to renal neural functions, applicants believe that the neuromodulation may at least partially denervate the patient's kidney(s). This may result in increased urine output, decreased plasma renin levels, decreased tissue (e.g., kidney) and/or urine catecholamines, renal catecholamine (e.g., norepinephrine) spillover, increased urinary sodium excretion, and/or controlled blood pressure. Furthermore, applicants believe that these or other changes may prevent or treat congestive heart failure, hypertension, myocardial infarction, renal disease, contrast nephropathy, other renal system diseases, and/or other renal or cardio-renal anomalies for a period of months (e.g., potentially up to six months or more).

The methods and apparatus described herein could be used to modulate efferent or afferent nerve signals, as well as combinations of efferent and afferent nerve signals. Neuromodulation in accordance with several embodiments of the present invention can be achieved without completely physically severing, i.e., without fully cutting, the target neural fibers. However, it should be understood that such neuromodulation may functionally achieve results analogous to physically severing the neural fibers even though the fibers may not be completely physically severed.

The apparatus described herein additionally may be used to quantify the efficacy, extent or cell selectivity of PEF therapy to monitor and/or control the therapy. When a pulsed electric field initiates electroporation, the impedance of the electroporated tissue begins to decrease and the conductivity of the tissue begins to increase. If the electroporation is reversible, the electrical parameters of the tissue will return to baseline values or approximate baseline values after terminating the PEF. However, if the electroporation is irreversible, the changes in the electrical parameters of the tissue will persist after terminating the PEF. These phenomena may be utilized to monitor both the onset and the effects of PEF therapy. For example, electroporation may be monitored directly using conductivity measurements or impedance measurements, such as Electrical Impedance Tomography ("EIT"), electrical impedance or conductivity indices and/or other electrical impedance/conductivity measurements. Such electroporation monitoring data optionally may be used in one or more feedback loops to control delivery of PEF therapy.

In order to collect the desired monitoring data, additional monitoring electrodes optionally may be provided in proximity to the monitored tissue. The distance between such monitoring electrodes preferably would be specified prior to therapy delivery and used to determine conductivity from impedance or conductance measurements. For the purposes of the present invention, the imaginary part of impedance may be ignored such that impedance is defined as peak voltage divided by peak current, while conductance may be defined as the inverse of impedance (i.e., peak current divided by peak voltage), and conductivity may be defined as conductance per unit distance. Applicants have previously described methods and apparatus for monitoring PEF therapy and have provided illustrative PEF waveforms, for example, in co-pending U.S. patent application Ser. No. 11/233,814, filed Sep. 23, 2005, which has been incorporated herein by reference in its entirety.

Figure 5A:
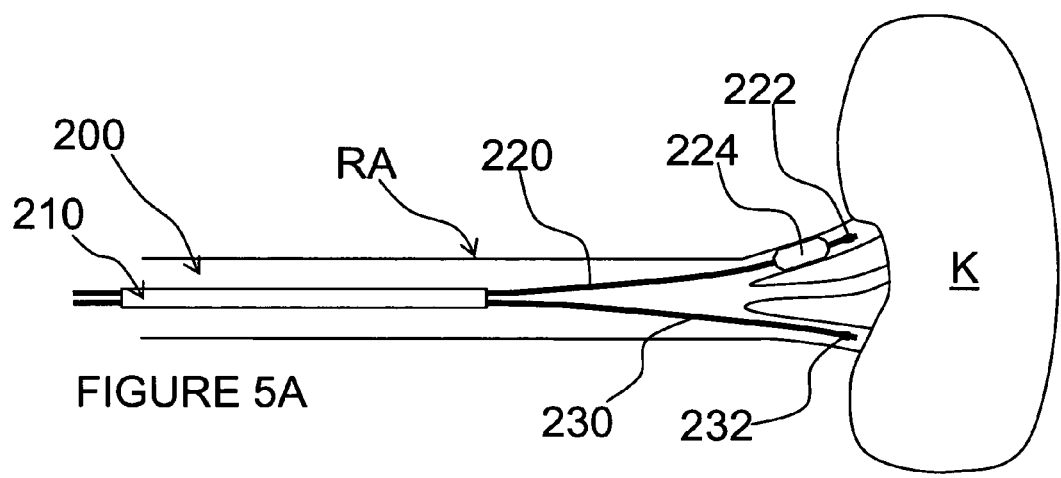
FIGS. 5A and 5B are schematic side views, partially in section, illustrating other examples of multi-vessel methods and apparatus for renal neuromodulation.
Figure 5B:
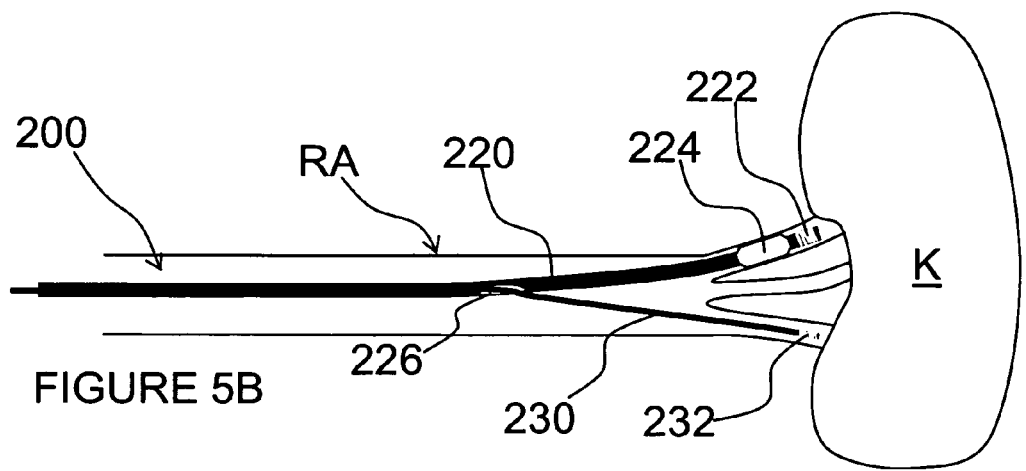
Figure 6:
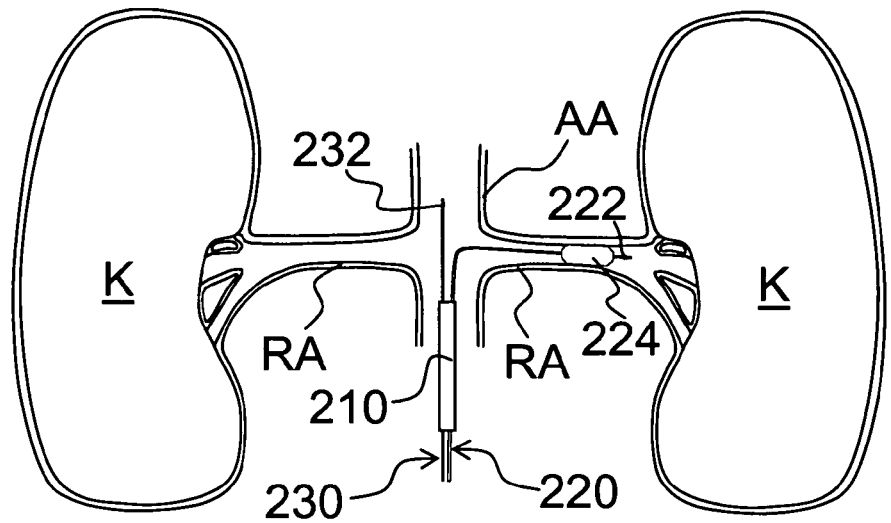
FIG. 6 is a schematic side view, partially in section, illustrating another method of utilizing the apparatus of FIG. 5A for multi-vessel renal neuromodulation.

Referring now to FIG. 6, another multi-vessel method of using the apparatus of FIG. 5A for renal neuromodulation is described. In addition to positioning electrodes within multiple branchings of the renal artery RA, a multi-vessel renal neuromodulation may be achieved with the electrodes positioned proximate to or within additional or alternative vessels. In FIG. 6, the first element 220 has been advanced through the guide catheter 210 to a position within the renal artery RA. The second element 230 has been advanced to a position within the abdominal aorta AA. A bipolar electrical field may be delivered between the first electrode 222 and the second electrode 232 to achieve renal neuromodulation.

Referring now to FIG. 6, another multi-vessel method of using the apparatus of FIG. 5A for renal neuromodulation is described. In addition to positioning electrodes within multiple branchings of the renal artery RA, a multi-vessel renal neuromodulation may be achieved with the electrodes positioned within additional or alternative vessels. In FIG. 6, the first element 220 has been advanced through the guide catheter 210 to a position within the renal artery RA. The second element 230 has been advanced to a position within the abdominal aorta AA. A bipolar electrical field may be delivered between the first electrode 222 and the second electrode 232 to achieve renal neuromodulation.

Figure 7A:
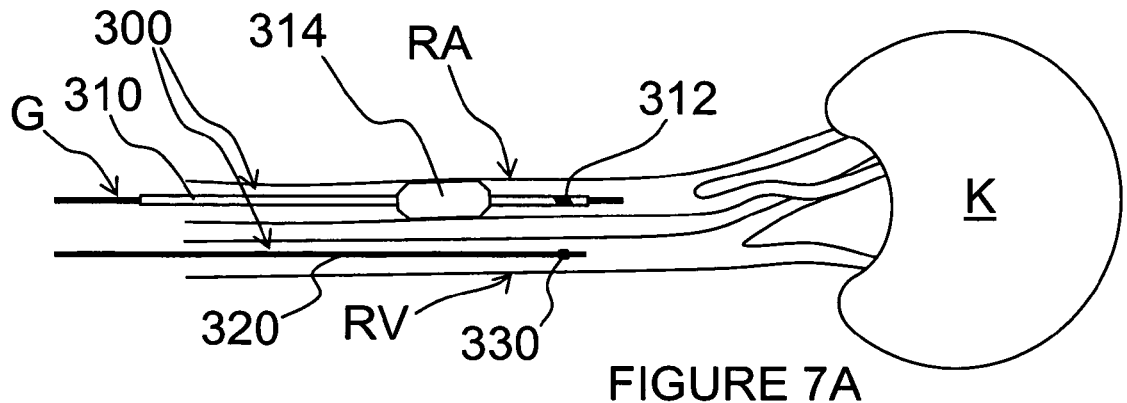
FIGS. 7A and 7B are schematic top views, partially in cross-section, illustrating additional examples of multi-vessel methods and apparatus for renal neuromodulation.
Figure 7B:
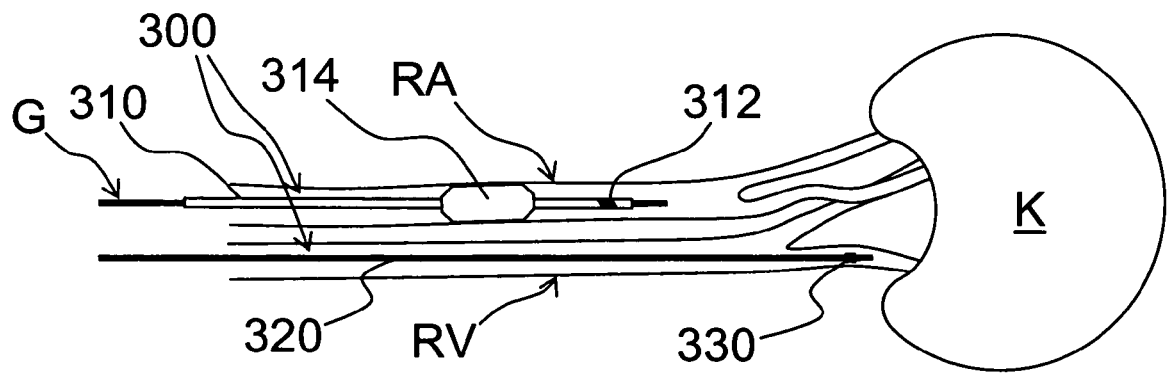

With reference now to FIGS. 7A and 7B, in addition to placement of the electrode(s) within (a) the renal artery RA, (b) branchings of the renal artery and/or (c) additional or alternative parts of the patient's arterial vasculature, multi-vessel renal neuromodulation may be achieved by locating one or more of the electrodes at least partially within the patient's venous vasculature. In FIG. 7, electrodes are positioned within both the renal artery RA and the renal vein RV of the patient. The PEF system 300 can comprise a catheter 310 positioned within the renal artery RA and an element 320 positioned within the renal vein RV. The catheter 310 comprises a first electrode 312 and an optional positioning element 314. The catheter 310 may be advanced into position within the renal artery, for example, over a guide wire G, then the positioning element may be expanded to center or otherwise position the electrode 312 within the vessel and/or to alter impedance within the vessel. The element 320 comprises a second electrode 330 that can be positioned within the renal vein, and the element 320 can optionally include a positioning element.

A bipolar electric field may be delivered between the first electrode 312 positioned within the renal artery and the second electrode 330 positioned within the renal vein to modulate target neural fibers that contribute to renal function via a multi-vessel approach. In FIG. 7A, electrodes 312 and 330 are relatively laterally aligned with one another. In FIG. 7B, the electrodes are laterally spaced apart from one another, which may facilitate preferential alignment of a bipolar electrical field delivered across the electrodes with the target neural fibers.

As discussed previously, a renal catecholamine (e.g., norepinephrine) spillover may indicate the extent of denervation or other renal neuromodulation achieved by methods in accordance with the present invention. A renal catecholamine spillover is defined as an imbalance between an amount of a renal catecholamine entering a kidney via a renal artery and an amount of the renal catecholamine exiting the kidney via a renal vein. For, example, neuromodulation may induce the kidney to excrete more norepinephrine into the renal vein than that which had entered the kidney via the renal artery. A baseline measurement of renal catecholamine spillover may be made prior to the renal neuromodulation. This baseline then may be compared to a measurement of the renal catecholamine spillover taken after the renal neuromodulation, and the difference may be attributed to the renal neuromodulation.

In order to measure the renal catecholamine spillover, blood may be drawn from the patient. For example, blood may be drawn from the renal artery and from the renal vein, and a differential in unit volume of the monitored renal catecholamine(s) between the arterial and venous blood may be used to quantify the renal catecholamine spillover and thus assess the degree of the renal neuromodulation. Such blood draws may, for example, be achieved by drawing blood through one or more guide catheters used to deliver a PEF system, such as the PEF system 300 of FIG. 7, to the renal artery and the renal vein.

Figure 8:
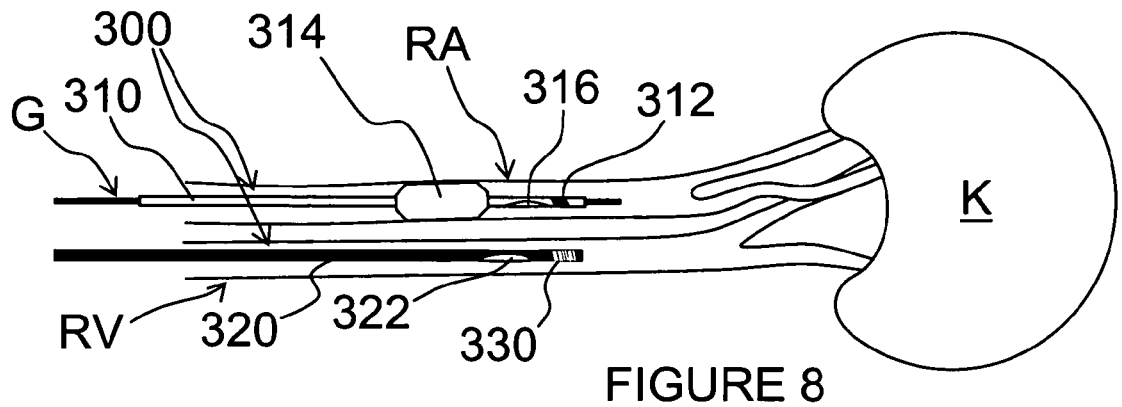
FIG. 8 is a schematic top view, partially in cross-section, illustrating an embodiment of the apparatus of FIG. 7 for assessing renal catecholamine spillover.

The blood draws additionally or alternatively may be made via one or blood ports integrated into the PEF system. In the embodiment of FIG. 8, the catheter 310 of the PEF system 300 of FIG. 7 comprises an arterial blood port 316 for drawing arterial blood, and the element 320 comprises a catheter having a venous blood port 322 for drawing venous blood. Additional and alternative methods and apparatus for monitoring of the renal catecholamine spillover will be apparent to those of skill in the art.

Figure 9:
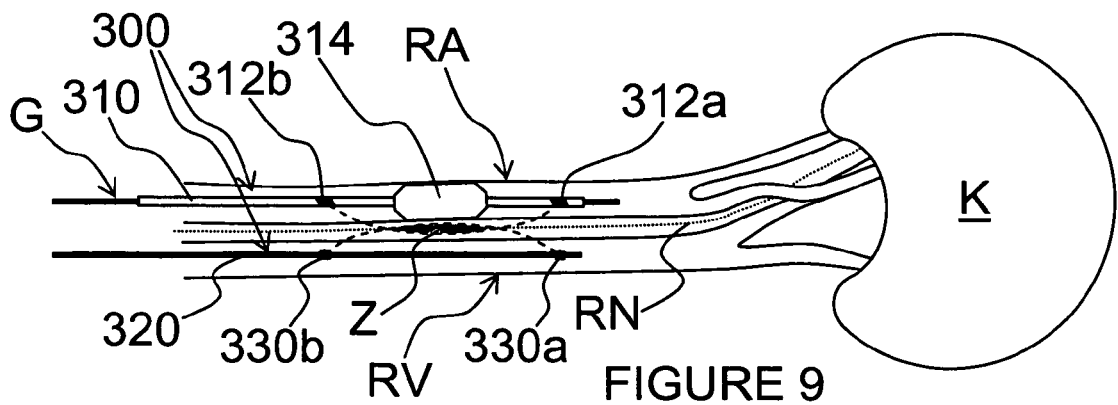
FIG. 9 is a schematic top view, partially in cross-section, illustrating an example of multi-vessel methods and apparatus for renal neuromodulation comprising overlapping bipolar electric fields.

In addition to delivery of a bipolar electric field between a first electrode positioned within a first vessel or vessel branch, and a second electrode positioned within a second vessel or vessel branch, a bipolar electric field may be delivered between first and second electrodes positioned solely within a single vessel or vessel branch. As seen in FIG. 9, a first bipolar electric field may be delivered between electrodes 312a and 312b positioned within a first vessel, such as the renal artery RA, while a second bipolar electric field may be delivered between electrodes 330a and 330b positioned within a second vessel, such as the renal vein RV. The first and second bipolar electric fields may be delivered in a manner that creates a zone of overlap Z between the bipolar fields.

Tissue positioned within the overlap zone Z may exhibit locally enhanced intensity of an induced electric field within the tissue, as compared to the intensity within tissue positioned outside of the overlap zone. When a target neural fiber, such as a target renal neural fiber RN, passes through the overlap zone Z, the locally enhanced intensity of the induced electric field within the target neural fiber may be of a magnitude sufficient to desirably modulate the neural fiber. Furthermore, the intensity of induced electric fields outside of the overlap zone desirably may be of magnitudes insufficient to cause damage to non-target tissues. Overlapping electric fields thus may reduce a risk of undesirable damage to non-target tissues, while locally providing an induced electric field of sufficient magnitude to achieve desired renal neuromodulation.

Figure 10:
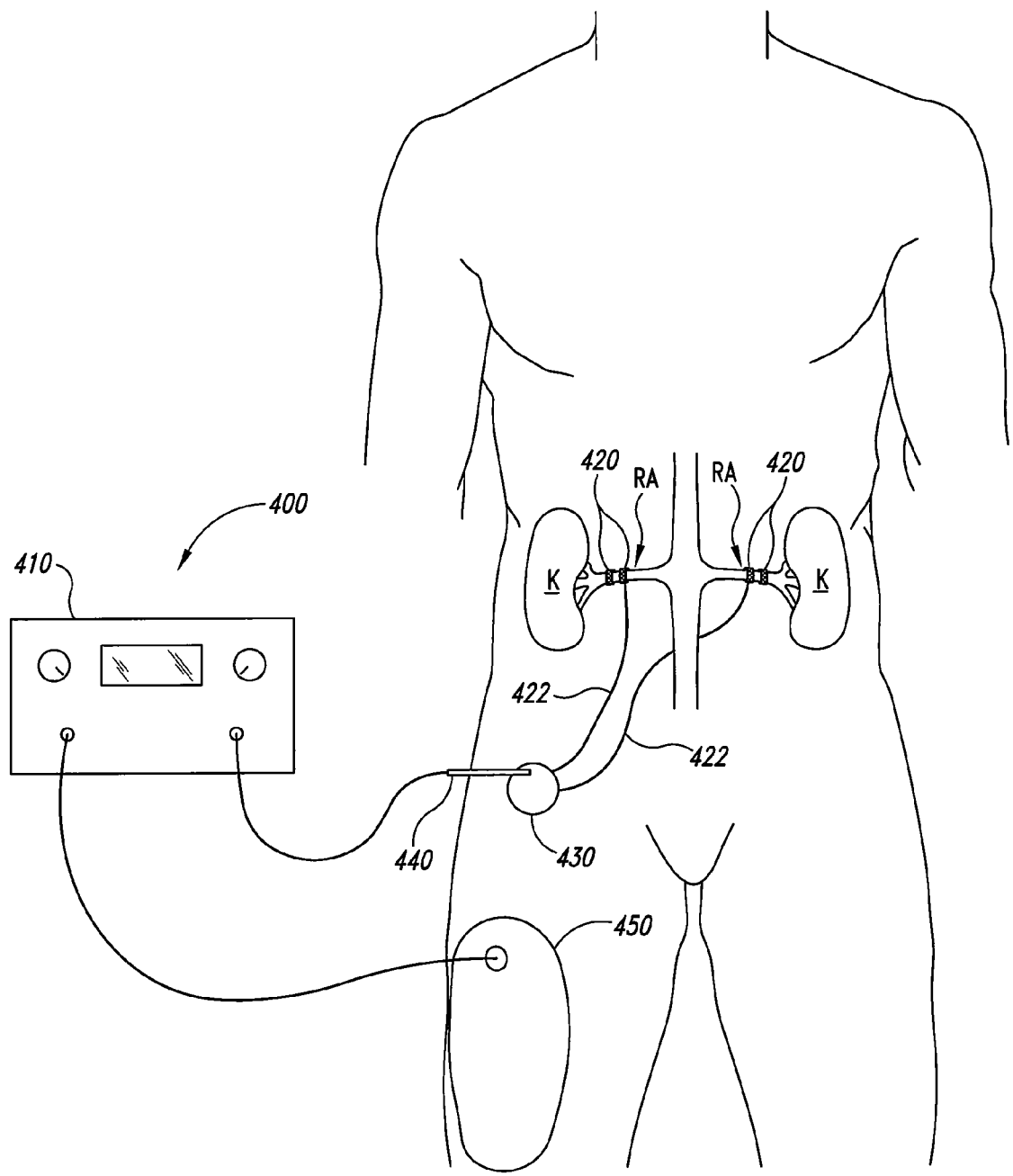
FIG. 10 is a schematic view illustrating a multi-vessel system for renal neuromodulation configured in accordance with another embodiment of the disclosure.

FIG. 10 illustrates a multi-vessel system 400 configured in accordance with another embodiment of the disclosure. The system 400 includes a generator or controller 410 electrically connected to electrodes 420 via leads 422. The electrodes 420 are placed around or near the renal artery RA or hilum, and the system 400 can be configured for unilateral or bilateral treatment. The electrodes 420 can include any of the various electrodes described herein. The leads 422 can be tunneled to a subcutaneous port or element 430. Alternatively, the subcutaneous port 430 may have multiple connecting points or docking points for different signals. A transcutaneous needle 440 may be used to pierce the skin and transmit RF signals to the electrodes 420 from the generator 410. A ground pad 450 may be attached externally to the patient (e.g., to the patient's leg, flank, back, side, etc.) and used as a return electrode when one or more of the electrodes deliver monopolar energy. Alternatively, the return electrode may be built into the subcutaneous port 430.

Although preferred illustrative variations of the present invention are described above, it will be apparent to those skilled in the art that various changes and modifications may be made thereto without departing from the invention. For example, one or more electrodes may be positioned in other parts of the patient's venous vasculature, such as within the patient's inferior vena cava or within vessel branchings of the patient's renal vein. It is intended in the appended claims to cover all such changes and modifications that fall within the true spirit and scope of the invention.

I claim:
1. A method for multi-vessel renal neuromodulation of a patient, the method comprising:
   placing a first electrode around or near a first renal artery of the patient and in proximity to a first neural fiber that innervates a first kidney of the patient;

placing a second electrode around or near a second renal artery of the patient and in proximity to a second neural fiber that innervates a second kidney of the patient; and passing electrical current through the first electrode and the second electrode to modulate the functions of the first and second neural fibers.

2. The method of claim 1 wherein passing electrical current through the first and second electrodes comprises creating a first electric field between the first electrode and a remote electrode and a second electric field between the second electrode and the remote electrode.

3. The method of claim 2 wherein the first and second electric fields are created simultaneously.

4. The method of claim 2 wherein the first and second electric field are created sequentially.

5. The method of claim 1 wherein passing electrical current through the first and second electrodes comprises creating a first electric field between the first electrode and a first remote electrode in the first renal artery and a second electric field between the second electrode and a second remote electrode in the second renal artery.

6. The method of claim 5 wherein the first and second electric fields are created simultaneously.

7. The method of claim 5 wherein the first and second electric fields are created sequentially.

8. The method of claim 1 wherein passing electrical current further comprises passing pulsed electrical current.

9. The method of claim 1 wherein modulating the functions of the first and second neural fibers further comprises at least partially denervating the first and second kidneys, respectively.

10. The method of claim 1 wherein modulating the functions of the first and second neural fibers further comprises inducing an effect in the first and second neural fibers chosen from the group consisting of irreversible electroporation, electrofusion, necrosis, apoptosis, gene expression alteration, cytokine up-regulation alteration, ablation and combinations thereof.

11. The method of claim 1 wherein modulating the functions of the first and second neural fibers further comprises thermally modulating the functions of the first and second neural fibers.

12. The method of claim 1 wherein modulating the functions of the first and second neural fibers further comprises, on average during passage of the electrical current, modulating the functions of the first and second neural fibers substantially athermally.

13. The method of claim 1 wherein modulating the functions of the first and second neural fibers further comprises treating a medical condition afflicting the patient.

14. The method of claim 13 wherein treating the medical condition afflicting the patient further comprises treating a medical condition chosen from the group consisting of heart failure, hypertension, myocardial infarction, renal disease, chronic renal failure, contrast nephropathy and combinations thereof.

15. The method of claim 1, further comprising altering impedance in the first renal artery or the second renal artery before passage of the electrical current.

16. The method of claim 15 wherein altering impedance further comprises temporarily altering blood flow within the first renal artery or the second artery.

17. The method of claim 1, further comprising monitoring a change in a renal catecholamine spillover in response to passing electrical current through the first electrode and the second electrode.

18. The method of claim 1 wherein:

placing a first electrode around or near a first renal artery of the patient comprises placing a first electrode within the first renal artery of the patient; and placing a second electrode around or near a second renal artery of the patient comprises placing a second electrode within the second renal artery of the patient.

19. The method of claim 1 wherein modulating the functions of the first and second neural fibers further comprises altering at least one of urine production, fluid retention, renin secretion, waste excretion, sodium retention, systemic vasoconstriction, renal function, heart function, and blood pressure in the patient.

20. The method of claim 1 wherein:

placing a first electrode around or near a first renal artery comprises placing a first cuff electrode around at least a portion of the first renal artery; and placing a second electrode around or near a second renal artery comprises placing a second cuff electrode around at least a portion of the second renal artery.

21. A method for a renal neuromodulation of a patient, the method comprising:

placing a first electrode within a first vessel of a patient at least substantially proximate to a neural fiber that contributes to a function of a kidney of the patient;

placing a second electrode within a second vessel of the patient, wherein the second vessel is a different vessel than the first vessel; and delivering an electric field between the first electrode and the second electrode and modulating the function of the neural fiber.

22. The method of claim 21 wherein placing the first electrode within the first vessel further comprises placing the first electrode in a first vessel of a renal vasculature of the patient.

23. The method of claim 22, wherein placing the second electrode within the second vessel further comprises placing the second electrode in a second vessel of the renal vasculature of the patient, the second vessel being a different vessel of the renal vasculature than the first vessel.

24. The method of claim 23 wherein placing the second electrode within the second vessel of the renal vasculature of the patient further comprises placing the second electrode in a second vessel branching of the renal vasculature.

25. The method of claim 21 wherein placing the first electrode within the first vessel and the second electrode within the second vessel further comprises placing the first electrode and the second electrode in different vessels of the patient chosen from the group consisting of a renal artery, renal artery branchings, a renal vein, renal vein branchings, an inferior vena cava, an abdominal aorta, renal vasculature, venous vasculature, arterial vasculature, and combinations thereof.

26. The method of claim 21, wherein placing the first electrode within the first vessel and placing the second electrode within the second vessel further comprises placing the first electrode and the second electrode in different vessels of the patient chosen from the group consisting of the renal artery, renal artery branchings, a renal vein, renal vein branchings, an inferior vena cava, an abdominal aorta, renal vasculature, venous vasculature, arterial vasculature, and combinations thereof.

27. The method of claim 21, further comprising monitoring a change in a renal catecholamine spillover in response to delivering an electric field between the first electrode and the second electrode.

28. The method of claim 21 wherein:
placing a first electrode within a first vessel of the patient comprises placing a first electrode within a first blood vessel corresponding to a first kidney of the patient; and
placing a second electrode within a second vessel of the patient comprises placing a second electrode within a second blood vessel corresponding to a second kidney of the patient.

29. The method of claim 28 wherein:
placing a first electrode within a first blood vessel corresponding to a first kidney of the patient comprises placing a first electrode within a first renal artery of the patient; and
placing a second electrode within a second blood vessel corresponding to a second kidney of the patient comprises placing a second electrode within a second renal artery of the patient.

30. The method of claim 21 wherein the electric field is a first electric field and the first vessel is a renal artery, and wherein the method further comprises:
placing a third electrode within the renal artery and laterally spaced apart from the first electrode along a lengthwise dimension of the renal artery; and
delivering a second electric field between the first electrode and the third electrode such that the resulting second electric field is generally aligned with a longitudinal axis of the renal artery and modulates the function of the neural fiber.

31. The method of claim 21 wherein modulating the function of the neural fiber further comprises at least partially denervating the kidney of the patient.

* * * * *